(12) United States Patent
Thompson

(10) Patent No.: US 6,695,802 B1
(45) Date of Patent: Feb. 24, 2004

(54) EAR CLEANER DEVICE

(76) Inventor: Annette F. Thompson, 13172 Acacia Dr., Grand Haven, MI (US) 49417

( * ) Notice: Subject to any disclaimer, the term of this patent is extended or adjusted under 35 U.S.C. 154(b) by 0 days.

(21) Appl. No.: 10/282,213

(22) Filed: Oct. 29, 2002

(51) Int. Cl.[7] .............................................. A61M 35/00
(52) U.S. Cl. ............................................ 604/1; 604/11
(58) Field of Search ........................ 604/1–3, 11, 14; 401/7; 600/38

(56) References Cited

U.S. PATENT DOCUMENTS 5,632,756 A * 5/1997 Kruglick ..................... 606/162
5,715,850 A * 2/1998 Markgraaf ................... 132/333
5,807,301 A * 9/1998 Nadam ........................... 604/1
6,080,126 A * 6/2000 Zygmont et al. ............... 604/1

FOREIGN PATENT DOCUMENTS

WO    WO 03/043528 A2 * 5/2003

* cited by examiner

Primary Examiner—Weilun Lo
Assistant Examiner—Jacqueline F Stephens

(57) ABSTRACT

An ear cleaner device for cleaning the wax and dirt from a user's ear. The ear cleaner device includes an elongate flexible support member; and also includes a pair of conical-shaped ear cleaning members being attached to the elongate flexible support member and being adapted to clean a user's ear canal.

6 Claims, 1 Drawing Sheet

EAR CLEANER DEVICE

BACKGROUND OF THE INVENTION

1. Field of the Invention

The present invention relates to ear cleaners and more particularly pertains to a new ear cleaner device for cleaning the wax and dirt from a user's ear.

2. Description of the Prior Art

The use of ear cleaners is known in the prior art. More specifically, ear cleaners heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 5,807,301; 2,511,557; 4,820,259; 5,147,288; and U.S. Pat. No. Des. 364,007.

While these devices fulfill their respective, particular objectives and requirements, the aforementioned patents do not disclose a new ear cleaner device. The prior art includes balls of cotton attached to ends of sticks and also includes thimble-like members being fitted upon a user's fingertip.

SUMMARY OF THE INVENTION

The general purpose of the present invention, which will be described subsequently in greater detail, is to provide a new ear cleaner device which has many of the advantages of the ear cleaners mentioned heretofore and many novel features that result in a new ear cleaner device which is not anticipated, rendered obvious, suggested, or even implied by any of the prior art ear cleaners, either alone or in any combination thereof. The present invention includes an elongate flexible support member; and also includes a pair of conical-shaped ear cleaning members being attached to the elongate flexible support member and being adapted to clean a user's ear canal. None of the prior art includes the combination of the elements of the present invention.

There has thus been outlined, rather broadly, the more important features of the ear cleaner device in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

It is an object of the present invention to provide a new ear cleaner device which has many of the advantages of the ear cleaners mentioned heretofore and many novel features that result in a new ear cleaner device which is not anticipated, rendered obvious, suggested, or even implied by any of the prior art ear cleaners, either alone or in any combination thereof.

Still another object of the present invention is to provide a new ear cleaner device for cleaning the wax and dirt from a user's ear.

Still yet another object of the present invention is to provide a new ear cleaner device that is easy and convenient to set up and use.

Even still another object of the present invention is to provide a new ear cleaner device that gives the user better control of the ear cleaning member than with traditional cotton swabs since the user guides the ear cleaning member with one's fingertip.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
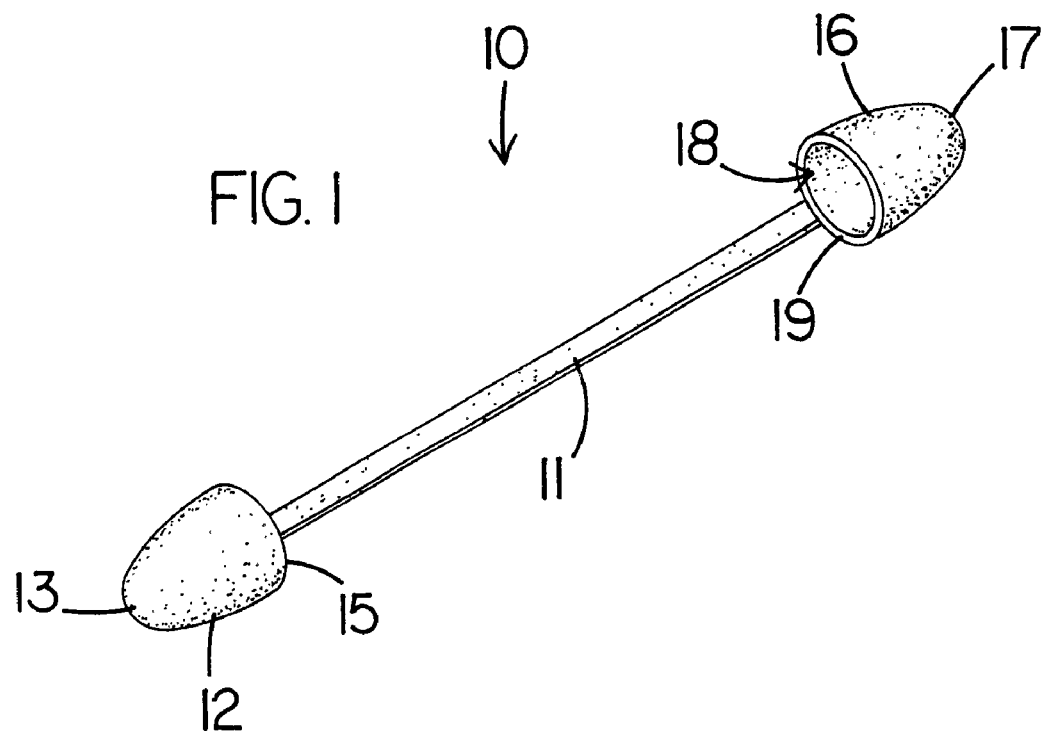
FIG. 1 is a perspective view of a new ear cleaner device according to the present invention.
Figure 2:
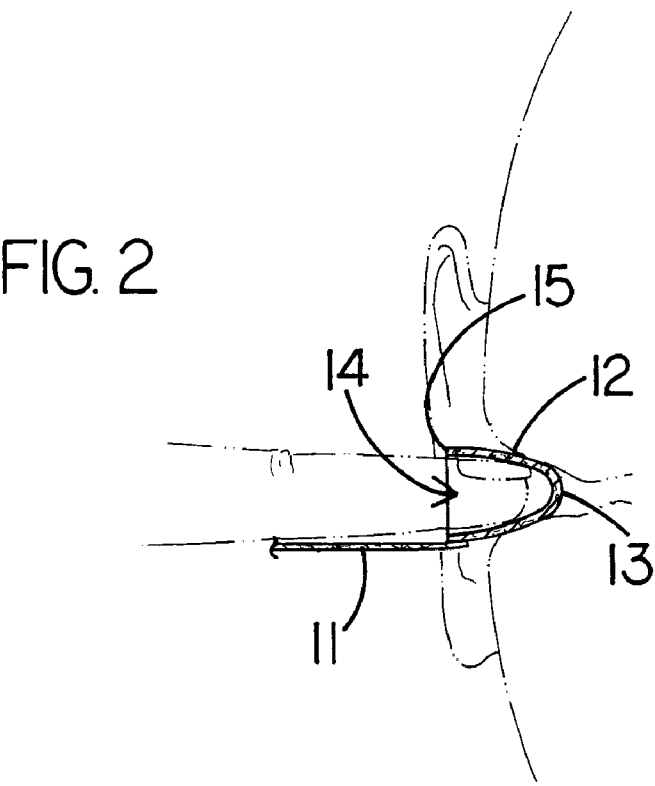
FIG. 2 is a cross-sectional view of the present invention.

With reference now to the drawings, and in particular to FIGS. 1 through 2 thereof, a new ear cleaner device embodying the principles and concepts of the present invention and generally designated by the reference numeral 10 will be described.

As best illustrated in FIGS. 1 through 2, the ear cleaner device 10 generally comprises an elongate flexible support member 11. The elongate flexible support member 11 is generally a stick made of cotton material and has a length of approximately 5 inches.

A pair of conical-shaped ear cleaning members 12,16 are conventionally attached to the elongate flexible support member 11 and are adapted to clean a user's ear canal. Each of the conical-shaped ear cleaning members 12,16 has a parabolic-shaped outer end 13,17 and also has an open end 14,18. Each of the conical-shaped ear cleaning members 12,16 has a rim 15,19 at the open end 14,18 thereof. The elongate flexible support member 11 has ends which are securely and conventionally attached to the rims 15,19 of the conical-shaped ear cleaning members 12,16. The conical-shaped ear cleaning members 12,16 are disposed with the open ends 14,18 facing one another and with the parabolic-shaped outer ends 13,17 facing away from one another. The conical-shaped ear cleaning members 12,16 are adapted to allow a user's fingertip to be extended through the open ends 14,18 thereof, and are adapted to fit about the user's fingertip. Each of the conical-shaped ear cleaning members 12,16 is made of cotton material and has a diameter of between ½ inch to ¾ inch.

In use, the user extends one's fingertip in one of the conical-shaped ear cleaning members 12,16 through the open end 14,18 thereof and places the fingertip-supported conical-shaped ear cleaning member 12,16 in one's ear and partially in one's ear canal to clean out wax and dirt which may have built up in one's ear. The user can hold onto the elongate flexible support member to better control the conical-shaped ear cleaning member 12,16 and prevent the conical-shaped ear cleaning member 12,16 from coming off one's fingertip during the use thereof.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the ear cleaner device. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An ear cleaner device comprising: an elongate flexible support member; and a pair of conical-shaped ear cleaning members being attached to said elongate flexible support member and being adapted to clean in an ear canal, wherein each of said conical-shaped ear cleaning members has a parabolic-shaped outer end and also has an open end and are adapted to allow a user's fingertip to be extended through said open ends thereof, and adapted to fit about the user's fingertip.

2. An ear cleaner device as described in claim 1, wherein said elongate flexible support member is generally a stick made of cotton material and has a length of approximately 5 inches.

3. An ear cleaner device as described in claim 1, wherein each of said conical-shaped ear cleaning members has a rim at said open end thereof.

4. An ear cleaner device as described in claim 3, wherein said elongate flexible support member has ends which are securely attached to said rims of said conical-shaped ear cleaning members.

5. An ear cleaner device as described in claim 4, wherein said conical-shaped ear cleaning members are disposed with said open ends facing one another and with said parabolic-shaped outer ends facing away from one another.

6. An ear cleaner device as described in claim 1, wherein each of said conical-shaped ear cleaning members is made of cotton material and has a diameter of between ½ inch to ¾ inch.

* * * * *